US00PP31315P2

(12) United States Plant Patent
Bedard

(10) Patent No.: US PP31,315 P2
(45) Date of Patent: Jan. 7, 2020

(54) ***GRANDIFLORA* ROSE PLANT NAMED 'WEKGRASUCEJUC'**

(50) Latin Name: *Rosa hybrida*
Varietal Denomination: WEKgrasucejuc

(71) Applicant: Early Morning, LLC, Pomona, CA (US)

(72) Inventor: Christian Bedard, Rancho Cucamonga, CA (US)

(73) Assignee: Early Morning, LLC, Lawrenceburg, IN (US)

( * ) Notice: Subject to any disclaimer, the term of this patent is extended or adjusted under 35 U.S.C. 154(b) by 0 days.

(21) Appl. No.: 16/350,681

(22) Filed: Dec. 19, 2018

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./130, 137
See application file for complete search history.

(56) References Cited

U.S. PATENT DOCUMENTS

PP23,476 P2 3/2013 Carruth

OTHER PUBLICATIONS

"Rosa 'Ausmary' Mary Rose", http://missouribotanicalgarden.org/PlantFinder/PlantFinderDetails, Missouri Botanical Garden website, accessed by client Mar. 8, 2019.
Weeks Roses, "Award Winning", Wholesale Rose Catalog, 84 pages, 2016.

*Primary Examiner* — Susan McCormick Ewoldt
(74) *Attorney, Agent, or Firm* — McKee, Voorhees & Sease, PLC

(57) ABSTRACT

A new variety of Grandiflora rose suitable for garden decoration, having flowers of medium pink coloration.

1 Drawing Sheet

Classification: The present invention relates to a new *Rosa hybrida* plant.

Variety denomination: The new plant has the varietal denomination 'WEKgrasucejuc'.

BACKGROUND OF THE INVENTION

This invention relates to a new and distinct variety of Grandiflora Rose. It has as its seed parent the variety known as 'WEKmerewby' (U.S. Plant Pat. No. 23,476) and a non-disseminated seedling of my creation as its pollen parent with the following genetic origin 'Sunset Celebration' x 'Julia Child'.

SUMMARY OF THE INVENTION

Among the features which distinguish the new variety from other presently available and commercial rose cultivars known to the inventor are the following combinations of characteristics: its elegant old-fashioned flowers of medium pink coloration, its excellent color stability throughout the life of the flowers and its abundant blooms. The plant has an upright somewhat spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKgrasucejuc' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKmerewby' by the following combination of characteristics: whereas 'WEKgrasucejuc' bears very double flowers (about 36 to 50 petals) of medium pink coloration, 'WEKmerewby' bears double flowers of saturate rose pink coloration with significantly lesser petalage (about 26 to 38 petals). The new variety has an upright somewhat spreading tall growing habit (about 140 to about 175 cm. in height), whereas the seed parent has an upright significantly taller growing habit (about 170 to about 190 cm. in height).

The new variety may be distinguished from its pollen parent, a non-disseminated seedling of my creation by the following combination of characteristics: whereas 'WEKgrasucejuc' bears very double flowers (about 36 to 50 petals) of medium pink coloration, the non-disseminated seedling bears double flowers of golden yellow coloration with significantly lesser petalage (about 25 to 32 petals). The new variety has an upright somewhat spreading tall growing habit (about 140 to about 175 cm. in height), whereas the pollen parent has an upright moderately spreading significantly shorter growing habit (about 120 to about 135 cm. in height).

COMPARISON WITH THE CLOSEST COMMERCIALLY AVAILABLE CULTIVAR

The new variety may be distinguished from its closest commercially available cultivar, 'AUSmary' (not patented) by the following combination of characteristics: whereas 'WEKgrasucejuc' bears very double flowers (about 36 to 50 petals) with slight tea to apple-like fragrance, 'AUSmary' bears double flowers with strong old rose, honey and almond blossom fragrance and with lesser petalage (about 26 to 40 petals). The new variety has an upright somewhat spreading tall growing habit (about 140 to about 175 cm. in height), whereas the closest commercially available cultivar has a bushy, compact and upright significantly shorter growing habit (about 120 to about 150 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October. Throughout this specification, color references and/or values are based upon the Colour Chart of The Royal Horticultural Society (2001) except where common terms of color definition are employed.

DESCRIPTION OF THE NEW VARIETY

The following description is of 3 to 4 year-old rose plants of the new variety grown outdoors in Wasco, Calif. in the month of December. Phenotypic expression may vary with environmental, cultural and climatic conditions, as well as differences in conditions of light and soil.

FLOWER

The new variety sometimes bears its flowers singly, sometimes in clusters of two to six per stem. Flowers may be borne in regular rounded clusters on strong medium to long stems (about 26 to about 85 cm.). The cluster ranges from about 11 to about 13.5 cm. in diameter. Outdoors, the plant blooms abundantly and nearly continuously during the growing season. The flowers have a slight tea to apple-like fragrance.

BUD

The peduncle is about 5 to about 7 cm. in length, of heavy caliper (about 0.4 to about 0.5 cm. in diameter), and erect. It is almost entirely smooth, with few hairs. Peduncle color is between 146B and 146C sometimes lightly suffused, especially on the side exposed to the sun, with near 178B.

Before the calyx breaks, the bud is about 2.2 to about 2.4 cm. in diameter at the widest point, about 2.8 to about 3.0 cm. in length, and pointed to ovoid in shape. The surface of the bud bears between 3 to 7 foliaceous appendages and glandular bloom, usually with foliaceous parts extending beyond the tip of the bud about ½ or more of its length. Bud color is between 146A and 146B sometimes lightly suffused, especially on the side exposed to the sun, with between 178A and 178B.

The sepals are 5 per flower, about 4 to about 5 cm. in length and about 1.2 to about 1.4 cm. in width at the widest point. The outer surface color of the sepal is between 146A and 146B sometimes lightly suffused, especially on the side exposed to the sun, with between 178A and 178B. The outer surface of the sepal is somewhat smooth and bears between 0 to 5 foliaceous appendages with some stipitate glands. The inner surface color of the sepal is between 138B to 138C broadly bordered by near 155D. After the sepals open, the inner surface color is sometimes lightly suffused, especially on the area exposed to the sun, with between 178B and 178C. The inner surface of the sepal is covered with fine wooly tomentum; sepal margins are entire and lined with many hairs. The sepals are permanent, and spear-shaped to recurved in shape with acute apices.

The receptacle of the flower is of medium length (about 0.8 to about 1.0 cm.) and average to heavy in caliper (about 1.2 to about 1.3 cm. in diameter). The receptacle is somewhat funnel shaped in form. Its surface is smooth with thick fleshy walls. The receptacle color is between 146A and 146B.

As the petals open (after the calyx breaks), the bud is about 3.1 to about 3.3 cm. in diameter at the widest point, about 3.5 to about 3.7 cm. in length, and globular in form. The color of the under surfaces of the newly opened petals is between 65A and 62B. At the point where the petal attaches, there is a somewhat large zone of between 3B and 3C. The color of the upper surfaces of the newly opened petals is between 62A and 62B. At the point where the petal attaches, there is a somewhat large zone of between 3B and 3C.

BLOOM

When fully open, the bloom ranges from about 8 to about 10 cm. in diameter. Petalage is very double with about 36 to 50 petals and about 3 to 12 petaloids irregularly arranged. When partially open, the bloom form is globular to cupped, and the petals are cupped with petal edges somewhat reflexed outward. When fully open, the bloom form is cupped and somewhat flattened, and the petals are loosely cupped to undulated with petal edges moderately reflexed outward.

PETALS

The substance of the petals is somewhat leathery and of medium thickness, with upper surfaces moderately shiny to satiny and under surfaces matte. The petals are about 4.0 to about 5.0 cm. in length and about 5.0 to about 6.0 cm. in width at the widest point. Petal margins are entire.

The outer petals are broadly round in shape with rounded apices.

The inner petals are broadly round in shape with rounded apices. Unlike the outer petals, the inner petals are often folded in leaving the center of the flower looking somewhat disorganized.

Petaloids are about 0.7 to about 1.5 cm. in length and about 0.1 to about 0.4 cm. in width at the widest point. Petaloids are shaped somewhat narrowly ovate to obovate with somewhat rounded to lacerated apices.

NEWLY OPENED FLOWER

The under surface color of the outer petals is between 65A and 62B. At the point where the petal attaches, there is a moderately large zone of between 3B and 3C. The upper surface color of the outer petals is between 62A and 62B. At the point where the petal attaches, there is a moderately large zone of between 3A and 3B.

The under surface color of the intermediate and inner petals is between 63C and 64D. The upper surface color of the intermediate and inner petals is near 64D.

The under and upper surface colors of the petaloids are similar in coloration to the upper and under surfaces of the intermediate and inner petals.

The general tonality of the newly opened flower is near 64D.

THREE-DAY-OLD FLOWER

The under surface color of the outer petals is between 65A and 62B. At the point where the petal attaches, there is a moderately large zone of between 3A and 3B. The upper surface color of the outer petals is between 62A to 62B. At the point where the petal attaches, there is a moderately large zone of between 3B and 3C.

The under surface color of the intermediate and inner petals is between 63C and 64D. The upper surface color of the intermediate and inner petals is near 64D.

The under and upper surface colors of the petaloids are similar in coloration to the upper and under surfaces of the intermediate and inner petals.

The general tonality of the three-day-old flower is near 64D.

On the spent bloom, the petals usually drop off cleanly.

In December in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 85) and are arranged somewhat regularly about the pistils; some are mixed with petaloids and tucked in the calyx. The filaments are of medium to long length (about 0.9 to about 1.1 cm.) most with anthers. Filaments are between 5A and 6B in color. The anthers are of medium size for the class and all open approximately at the same time. Anther color when immature is near 14C on the external part and near 6D on the internal part. Anther color at maturity is near 167C on the external part and near 167D on the internal part. Pollen is moderate and near 163C in color.

FEMALE REPRODUCTIVE ORGANS

Pistils vary in number (average about 40). The styles are somewhat uneven, average in length (about 0.4 to about 0.6 cm.), average in caliper, and bunched to columnar. Stigma color is near 160D. Style color is near 157D on the lower third changing to near 186D on the upper portion. Ovaries are usually all enclosed in the calyx. The ovaries are of medium size and between 157C and 157D in color.

Hips have not been observed on this variety when grown in Wasco, Calif.

FOLIAGE

The compound leaves are usually comprised of three to seven leaflets and are borne abundantly. The five-leaflet leaves are about 11 to about 12 cm. in length and about 8.0 to about 9.0 cm. in width at the widest point, very leathery in texture on both sides, and glossy in finish on the upper side and matte in finish on the underside. The leaves have a pinnate venation pattern. The terminal leaflets are about 5.0 to about 5.5 cm. in length and about 3.4 to about 3.8 cm. in width at the widest point, shaped oval to ovate with subacute apices and round bases. Their margins are simply serrate.

The upper surface color of the mature leaf is between 147A and 147B. The under surface color of the mature leaf is near 147B. The under and upper colors of the leaf veins on the mature leaf are similar in coloration to the upper and under surfaces colors of the mature leaf. The upper surface color of the young leaf is between 147B and 146B, sometimes lightly suffused with near 178A. The under surface color of the young leaf is near 146B, sometimes lightly suffused with near 178A. The under and upper colors of the leaf veins on the young leaf are similar in coloration to the upper and under surfaces colors of the young leaf.

The rachis is about 5.0 to about 5.5 cm. in length, about 0.1 to about 0.15 cm in width at the widest point, and rough. The upper side is moderately grooved with few stipitate glands on the edges of the grooves. The under side of the rachis is rough with a few stipitate glands and medium sized prickles. The rachis color is near 146C on the under side and near 147B on the upper side, sometimes lightly suffused on the young leaves with near 178B.

The stipules are about 1.3 to about 1.5 cm. in length and of medium width (about 0.5 to about 0.7 cm.) with medium length straight points that usually turn out at an angle of less than 45 degrees. The under and upper surface color of the stipule is between 147C and 146D. The upper and under surfaces of the stipules are smooth in texture.

The petiole is somewhat light in caliper and smooth. The upper side is moderately grooved with few stipitate glands on the edges of the grooves. The under side of the petiole is smooth, The petiole is about 0.3 to about 0.7 cm. in length and about 0.1 to about 0.15 cm in width at the widest point. The petiole color is near 146C on the under side and near 147B on the upper side, sometimes lightly suffused on the young leaves with near 178B.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright somewhat spreading tall growing habit (about 140 to about 175 cm. in height and about 110 to about 155 cm. spread at the widest point), with full branching. It displays vigorous growth and the canes are of medium to heavy caliper for the class (about 1.8 to about 2.7 cm. in diameter at the widest point).

The color of the major stems is between 146B and 146C. The major stems are rough in texture and they bear several large prickles that are about 0.5 to about 0.7 cm. in length. The large prickles are almost straight and angled slightly downward with a medium length and rounded base; prickle color is near 165D. The major stem bears few small prickles of similar shape and coloration.

The color of the branches is between 146A and 147B. The branches are rough in texture and they bear many large prickles which are of similar size and shape to the large prickles on the major stems; prickle color is near 165D. The branches bear few small prickles of similar shape and coloration.

The color of the new shoots is between 146C and 146D, sometimes lightly suffused with near 178B. The new shoots are rough in texture and they bear several large prickles which are of similar size and shape to the large prickles on the major stems; prickle color is near 170C. The shoots bear few small prickles of similar shape and coloration.

I claim:

1. A new and distinct Grandiflora rose plant of the variety substantially as described and illustrated herein.

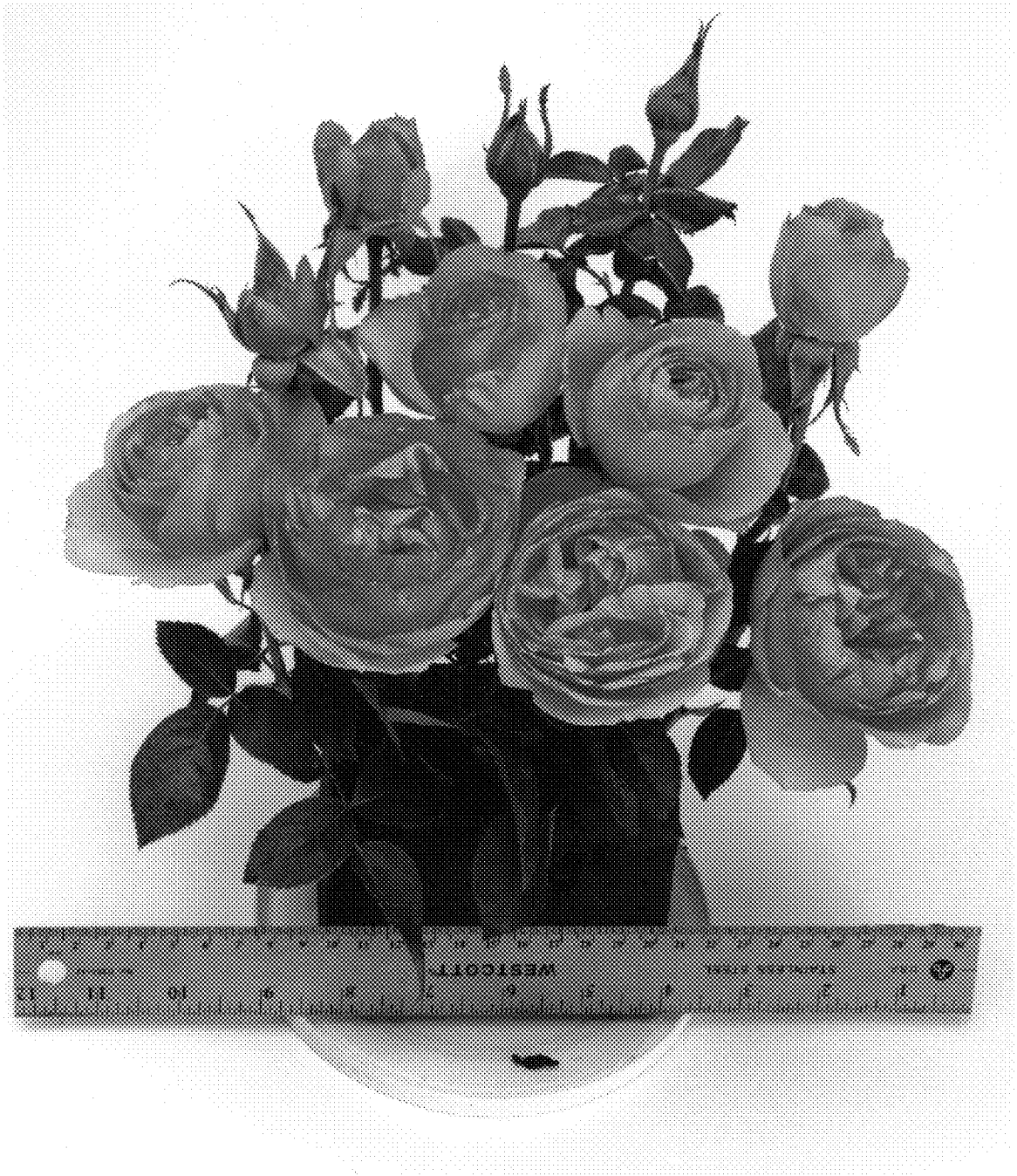

* * * * *